United States Patent [19]

Pfeiler et al.

[11] 4,411,012

[45] Oct. 18, 1983

[54] DIAGNOSTIC RADIOLOGY INSTALLATION

[75] Inventors: Manfred Pfeiler, Erlangen; Edgar Tschunt, Rathsberg, both of Fed. Rep. of Germany

[73] Assignee: Siemens Aktiengesellschaft, Berlin & Munich, Fed. Rep. of Germany

[21] Appl. No.: 234,412

[22] Filed: Feb. 13, 1981

[30] Foreign Application Priority Data

Mar. 20, 1980 [DE] Fed. Rep. of Germany ....... 3010780

[51] Int. Cl.³ .............................................. G03B 41/16
[52] U.S. Cl. .......................................... 378/17; 378/4; 378/146
[58] Field of Search .............................. 378/4, 17, 146

[56] References Cited

U.S. PATENT DOCUMENTS

| 4,138,721 | 2/1979 | Boyd | 378/17 |
| 4,174,481 | 11/1979 | Liebetruth | 378/20 |
| 4,179,100 | 12/1979 | Sashin et al. | 250/416 TV |

Primary Examiner—Craig E. Church
Attorney, Agent, or Firm—Hill, Van Santen, Steadman & Simpson

[57] ABSTRACT

In an exemplary embodiment, there is provided a patient support, a radiation measuring arrangement including a radiation source which generates at least one fan-shaped radiation beam, penetrating the radiography subject, and a radiation receiver which has an array of detectors which are connected to a signal processing circuit, and means for generating relative movement between the patient support and the radiation measuring arrangement in a longitudinal direction of the support, for the generation of a shadow image several radiation directions are generated so that a plurality of intersection points of the radiation paths result within an image exposure region. The signal processing circuit determines the radiation transparency in the patient for every intersection point of a plane parallel to the patient support.

2 Claims, 4 Drawing Figures

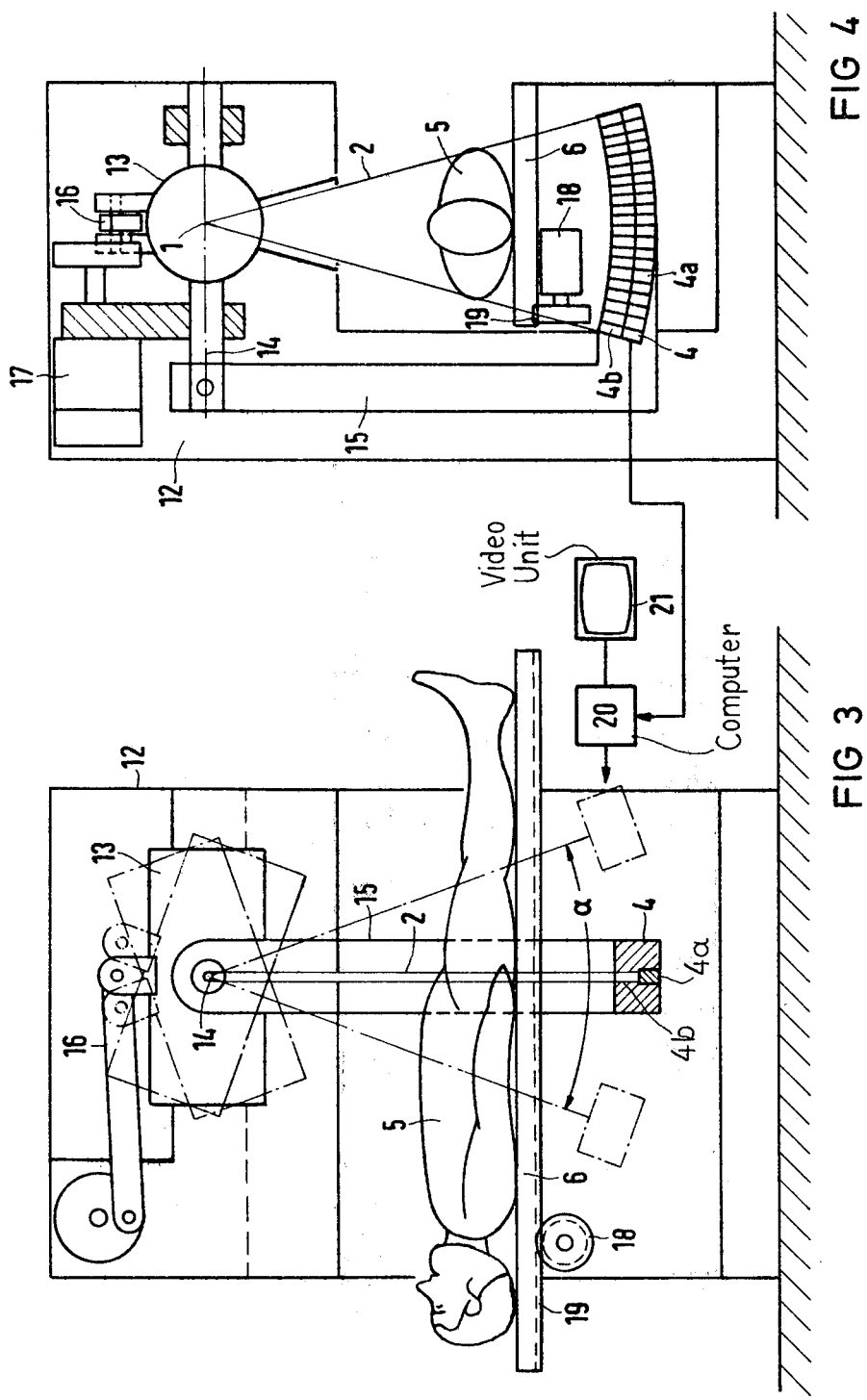

DIAGNOSTIC RADIOLOGY INSTALLATION

BACKGROUND OF THE INVENTION

The invention relates to a diagnostic radiology installation, comprising a patient support, a radiation measuring arrangement comprised of a radiation source, which generates at one least fan-shaped radiation beam penetrating the radiography subject, and disposed transversely to the patient support, and comprised of a radiation receiver which is formed by an array of detectors which are connected to a signal processing circuit, and means for effecting a relative movement between the patient support and the radiation measuring arrangement in the longitudinal direction of the support for generation of a shadow image from the detector output signals by means of the signal processing circuit.

A diagnostic radiology installation of this type is described in the German O.S. No. 26 13 809 (U.S. Pat. No. 4,174,481). The known diagnostic radiology installation relates to a computer tomograph which is supplemented with means which permit the preparation of a shadow image of a specific region of a patient. For the preparation of the computer tomogram, the measuring arrangement is rotated about the longitudinal axis of the support or about an axis which is parallel thereto. From the output signals of the detectors, a computer calculates the attenuation values of image points arranged in a matrix, which can then be reproduced as an image of the examined transverse layer of the patient. For the generation of a shadow image, the measuring arrangement is locked against rotation and a relative movement between the patient support and the measuring arrangement in the longitudinal direction of the support takes place. A shadow image thus contains, in superimposed form, all details of the irradiated radiography region. Since these details are superimposed on one another, (for example, in the case of observation of the chest, a superposition of the front and rear rib sections takes place), the image is of little significance in terms of information-content.

In order to improve x-ray shadow images, it is already known to form a sharp image of only one layer of the patient, parallel to the patient support, by fixedly coupling with one another the x-ray tube and an x-ray film cassette and pivoting this unit about a pivot axis lying in the desired layer. In this case, sharp images are produced on the x-ray film only of the details of the selected layer, whereas the remaining details are imaged in a blurry fashion. It is disadvantageous here that the secondary radiation grid, which must be aligned to the focus of the x-ray tube, on account of the necessary movement of the radiographic unit comprised of the x-ray tube and the x-ray film cassette, can exhibit only lamellae or leaves which extend in the direction of movement. There consequently results only incomplete stray radiation suppression.

SUMMARY OF THE INVENTION

The object underlying the invention resides in creating a diagnostic radiology apparatus of the type initially cited with which it is possible to prepare radiographs of desired layers of the patient, said layers being disposed parallel to the patient support whereby the effect of the stray radiation on the image quality is kept as low as possible.

In accordance with the invention, this object is achieved by virtue of the fact that means are present for generating several radiation directions, such that a plurality of intersection points of the radiation paths result within an image exposure region, and that the signal processing circuit is so designed that, for every intersection point of a plane parallel to the patient support, it determines the radiation transparency in the patient. In the case of the inventive diagnostic radiation installation, the stray radiation can be well suppressed by means of a collimator arranged in front of the radiation receiver. An x-ray shadow image of a layer parallel to the patient support can, in a simple fashion, be calculated by the signal processing circuit and reproduced on a video unit.

One embodiment of the invention is one wherein a radiation source is rigidly connected with the radiation receiver formed of a single detector array, and wherein the detector array is pivotable about the focus of the radiation source. In this case, the scanning of the image exposure region can proceed in such a fashion that, first a pivoting of the radiation measuring arrangement through a predetermined angle takes place, then a relative longitudinal movement between the radiation measuring arrangement and the patient support through a predetermined step takes place, then again a pivoting takes place, then again a relative movement, etc., takes place. Another variant is one wherein the radiation source emits several ray fans in different directions, each of which is received by a detector array, and that the radiation source and all detector arrays are stationarily arranged in the apparatus. In each case, a movement of the patient support suffices for the purpose of scanning the image exposure region.

The invention shall be explained in greater detail below on the basis of the accompanying drawing sheets; and other objects, features and advantages will be apparent from this detailed disclosure and from the appended claims.

BRIEF DESCRIPTION OF THE DRAWINGS

FIGS. 3 and 4 provide diagrammatic views of a diagnostic radiology installation according to the invention, taken from two mutually perpendicular directions.

DETAILED DESCRIPTION

Figure 1:
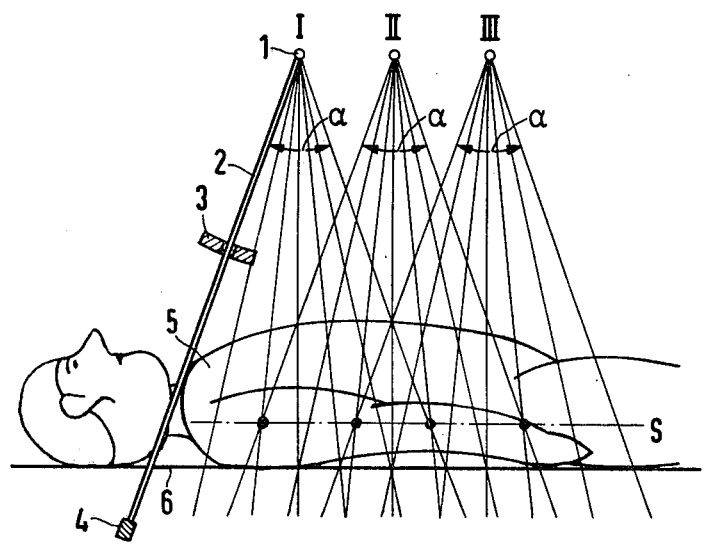
FIGS. 1 and 2 are diagrammatic elevational views providing schematic illustrations of two variants of the invention.

In FIG. 1, the focus 1 of an x-ray tube is illustrated which emits a fan-shaped x-ray beam 2 which is defined by means of a collimator or primary radiation diaphragm 3. The x-ray beam 2 is received by a detector array 4 which, for example, can be designed as an arcuate segment with a center of curvature at the focus 1. The detector array 4 can comprise 512 individual detectors. The measuring arrangement 1, 4, serves the purpose of scanning a patient 5 resting on a support 6 which is movable in its longitudinal direction.

The scanning of the image exposure region of the patient 5 proceeds in such a manner that, in the illustrated position I of the focus, the x-ray tube and the radiation receiver 4 are pivoted about the focus 1 through the angle $\alpha$. During the pivoting, in predetermined angular positions, the output signals of the individual detectors of the radiation receiver 4 are interrogated (or sampled). In FIG. 1, seven radiation paths are illustrated in which interrogation (or sampling) takes place. In practice, naturally, there will be substantially more radiation paths. Following the pivotal movement, a longitudinal movement of the x-ray tube and of the radiation receiver 4, which is rigidly connected therewith, takes place until the focus lies in the position II. In this position, a pivoting through the angle α and an interrogation (or sampling) corresponding to the previously described instance again takes place. Subsequently, the x-ray tube with the radiation receiver 4 is so moved that the focus occupies the position III. In this position, again a pivoting and a signal interrogation (or sampling), etc., takes place. The angle α can, for example, amount to 40°.

From FIG. 1 it is apparent that the individual radiation paths of the radiation beam 2, running transversely to the patient support 6, have a plurality of intersection points in the image exposure region of the patient 5, which intersection points result from the different radiation directions. By means of a signal processing circuit, which contains a computer, it is possible to determine and reproduce, as an image, the radiation transparency in the patient 5 for the intersection points lying in a plane S running parallel to the patient support 6. In this manner, one obtains an x-ray shadow image of a longitudinal layer of the patient. The computer thus processes the output signals of the individual detectors of the radiation receiver 4, which are designed as radiation-electric transducers.

In a second embodiment for effecting the described scanning procedure of FIG. 1, it is possible to dispense with the longitudinal movement of the radiation measuring arrangement 1, 4, if it is replaced by a longitudinal movement of the patient support 6 with the patient 5. In this case, it suffices if the measuring arrangement 1, 4, is pivotably mounted about the focus 1.

Figure 2:
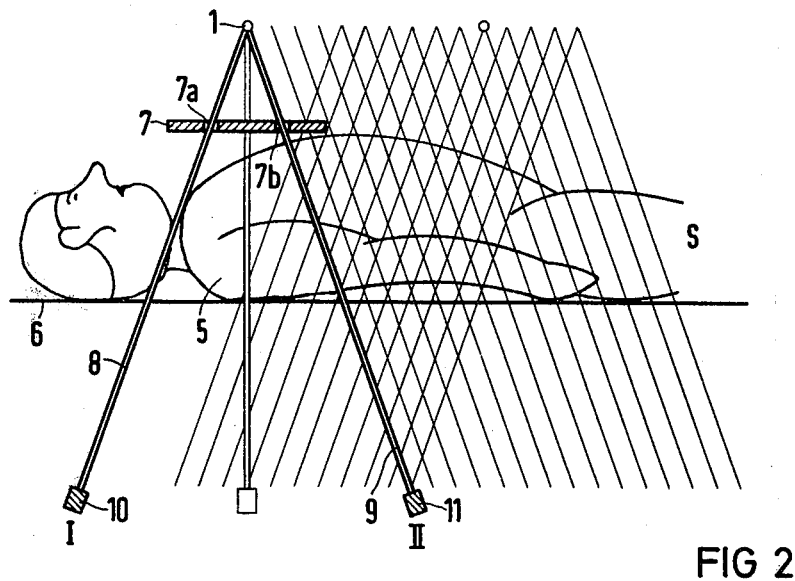

In the exemplary embodiment according to FIG. 2, a collimator (or primary radiation diaphragm) 7 is present which defines two fan-shaped x-ray beams 8, 9, which penetrate the patient 5 from different directions. Every radiation beam 8, 9, is received by one radiation receiver 10, 11, respectively, which again is comprised of a series of individual detectors, for example 512 individual detectors. In this case, the x-ray tube as well as the radiation receiver 10, 11, can be stationarily arranged in the apparatus. The scanning of the image exposure region can proceed by virtue of the fact that the patient support 6 with the patient 5 is moved a predetermined extent in its longitudinal direction. In this manner, as is illustrated in FIG. 2, one likewise obtains a plurality of intersection points which, in the described manner, form the basis for image production.

In the example according to FIG. 2, it is possible to control the apertures 7a and 7b in such a fashion that they are only then opened when the radiation generates the signals which also actually are usable for the purpose of image production. Thus, for example, the scanning operation can proceed from the illustrated position in such a manner that first only the x-ray beam 9 is present, and only when intersection points result in the patient 5, is the x-ray beam 8 established. At the end of the advance, the aperture 7b then first closes, and only thereafter does the aperture 7a close. The radiation exposure of the patient 5 can thereby be kept small.

In FIG. 2, the intersection points of the radiation paths are illustrated in that the focus 1 is illustrated as traveling and the patient support 6 is illustrated as stationary. This is indeed a possibility for scanning the image exposure region; however, as described above, in the example, the relative movement takes place in longitudinal direction of the support by virtue of the fact that only the patient support 6 is moved. Nothing is changed thereby regarding the position of the intersection points.

In FIGS. 3 and 4, orthogonal views of a diagnostic radiology installation according to the invention are illustrated by means of which the scanning movement, described as a second embodiment in conjunction with FIG. 1, can take place. On an apparatus frame 12, an x-ray tube 13 is pivotably mounted about a horizontal axis 14. The x-ray tube 13 is fixedly connected via an arm 15 with the radiation receiver 4. From FIG. 4 it is apparent that the radiation receiver is comprised of an array 4a of individual detectors in front of which a collimator 4b is arranged aligned with the focus 1.

Via a crank mechanism 16, which is driven by a motor 17, FIG. 4, the x-ray tube 13 is pivotal about the axis 14, which passes through the focus 1, through the angle α illustrated in FIG. 3. The radiation receiver 4 participates in this pivotal movement, and can thus be pivoted into the positions illustrated by dot dash lines in FIG. 3. The longitudinal movement of the support proceeds by means of a motor 18 which engages in a toothed rack 19 on the lower side of the patient support 6. In addition, a computer 20 is present which is connected to the radiation receiver 4 and computes the respective x-ray shadow image of the selected layer and effects its reproduction on a video unit 21. In FIG. 1, such a possible layer is, for example, illustrated and referenced with S. For the computation of the image of this layer, the intersection points are utilized which are heavily marked in FIG. 1.

In the example according to FIG. 1, it is also possible to rigidly connect only the collimator (or primary radiation diaphragm) 3 with the radiation receiver 4, comprised of a single detector array, and to arrange it pivotably about the focus 1 of the stationary x-ray tube.

It will be apparent that many modifications and variations may be effected without departing from the scope of the novel concepts and teachings of the present invention.

We claim as our invention:

1. A diagnostic radiology installation comprising a patient support extended in a longitudinal direction, a radiation measuring arrangement comprised of a radiation source, which generates at least one fan-shaped radiation beam penetrating the radiography subject and disposed transversely to the patient support, and of a radiation receiver which has an array of detectors which are connected to a signal processing circuit, means for effecting a relative movement between the patient support and the radiation measuring arrangment in the longitudinal direction of the support for generating a shadow image from the detector output signals by means of signal processing, means (16, 17, 18, 19) for generating several radiation directions are present, so that a plurality of intersection points of the radiation paths within an image exposure region result, and a signal processing circuit (20) coupled with said detectors for determining the radiation transparency in the patient (5) for every intersection point of a plane (S) parallel to the patient support (6), the radiation source (13) being rigidly connected with the radiation receiver (4) and being pivotal about the focus (1) of said radiation source.

2. A diagnostic radiology installation comprising a patient support extended in a longitudinal direction, a radiation measuring arrangement comprised of a radiation source, which generates at least one fan-shaped radiation beam penetrating the radiography subject and disposed transversely to the patient support, and of a radiation receiver which has an array of detectors which are connected to a signal processing circuit, means for effecting a relative movement between the patient support and the radiation measuring arrangement in the longitudinal direction of the support for generating a shadow image from the detector output signals by means of signal processing, means (16, 17, 18, 19) for generating several radiation directions are present, so that a plurality of intersection points of the radiation paths within an image exposure region result, and a signal processing circuit (20) coupled with said detectors for determining the radiation transparency in the patient (5) for every intersection point of a plane (S) parallel to the patient support (6), the radiation source emitting several ray fans (8, 9) at different directions, a detector array (10, 11) for receiving each ray fan, and the radiation source and all detector arrays (10, 11) being stationarily arranged.

* * * * *